United States Patent [19]

Sizto et al.

[11] Patent Number: 4,575,485
[45] Date of Patent: Mar. 11, 1986

[54] ULTRASONIC ENHANCED IMMUNO-REACTIONS

[75] Inventors: N. Chung Sizto, Union City; Cindy Gallup, Foster City, both of Calif.

[73] Assignee: Syntex (U.S.A.) Inc., Palo Alto, Calif.

[21] Appl. No.: 527,441

[22] Filed: Aug. 29, 1983

[51] Int. Cl.$^4$ .................... G01N 33/53; G01N 33/543
[52] U.S. Cl. ......................................... 435/7; 436/518; 436/536; 436/824
[58] Field of Search ...................... 435/7; 436/518, 536

[56] References Cited

U.S. PATENT DOCUMENTS 4,410,634 10/1983 Cooper et al. ........................ 435/7
4,477,576 10/1984 Deutsch et al. ...................... 435/7

FOREIGN PATENT DOCUMENTS 2624085 12/1972 Fed. Rep. of Germany .......... 435/7
144558 10/1980 German Democratic Rep. .... 435/7
150628 9/1981 German Democratic Rep. .... 435/7
0136163 8/1982 Japan ...................................... 435/7

OTHER PUBLICATIONS

High Technology, Mar. 1983, Perspectives: "Tiny Bubbles Promote Chemical Reactions".
Berezin et al., from Biomedical Applications of Immobilized Enzymes and Proteins, vol. 2, Ed. Chang, Plenum Press, NY, 1979, 237-251.

*Primary Examiner*—Christine M. Nucker
*Attorney, Agent, or Firm*—Theodore J. Leitereg

[57] ABSTRACT

Rates of binding between members of a specific binding pair, e.g., ligand-receptor, are greatly enhanced by short-term ultrasonication of an aqueous medium containing the specific binding pair. The enhanced rates find particular use in specific binding protein assays.

22 Claims, No Drawings

ULTRASONIC ENHANCED IMMUNO-REACTIONS

BACKGROUND OF THE INVENTION

1. Field of the Invention

There is a wide variety of situations where one is interested in the binding of a ligand and its receptor, particularly haptens and antigens with their respective antibodies. In many assays involving ligand-receptor binding, the concentrations of interest are extremely low and in view of the thermal lability of the reactants, elevated temperatures are precluded. In many instances, mechanical agitation, such as vortexing or rapid stirring, is precluded.

The problem is exacerbated when one of the members of the ligand-receptor pair is bound to a solid support. In effect, the diffusion rate for such a member is zero and one must depend on the diffusion of the other member of the pair for the combining reaction. Furthermore, with one of the members being a large protein, such as an antibody, the rate of diffusion is quite slow. Thus, in situations involving low rates of diffusion and low concentrations of one or both of the binding pair, it becomes important to find techniques to enhance the rate at which the two members of the binding pair react to form a complex.

2. Description of the Prior Art

See Berezin, et al., *Mechanosensitive and Sound-Sensitive Enzymatic Systems as Chemical Amplifiers of Weak Signals*, in "Immobilized Enzymes and Proteins," ed. Thomas Ming Swi Chang, Plenum Press, New York, Vol. 2, 1979, pps. 237-251 and *Methods and Phenomena*, Vol. 3, Pt. 2; "Ultra Sound; Its Applications in Medicine and Biology," Fry, Francis J., Ed., Elsevier, Amsterdam, Netherlands, 1978, 210. Stein, et al., *J. Inorg. Biochem.*, (1982) 16:71-7 describe the effect of sample preparation on analysis of superoxide dismutase activity and isoenzymes, where the effect of sonication is reported. Ishimori, et al., *J. Mol. Catal.*, (1981), 12:253-9 describe the acceleration of immobilized α-chymotrypsin activity with ultrasonic irradiation. Kashkooli, et al., *J. Acoust. Soc. Am.*, (1980) 67:1798-1801 describe the effects of ultrasound on catalase and malate dehydrogenase. Fischer, J. Ger. Appl No. 144,558 describes increasing the activity of immobilized enzymes by ultrasonic treatment of the organic carrier. Schmidt, P. (Ger. Appl. No. 150,628) describes the reactivation of immobilized enzymes by ultrasonic treatment. See also Chemical Abstracts 89:2794Y; 96:179390j; 96:138563Z; 95:146154m; 93:64760A; 92:142400d; 96:118157s. See also an article in *High Technology*, entitled "Perspectives," March, 1983.

SUMMARY OF THE INVENTION

Rates of complex formation between members of a specific binding pair are enhanced by the ultrasonication of a medium containing the members of the specific binding pair for a time sufficient to effectuate the enhancement. The method finds particular application in clinical assays particularly where one of the members is bound to a solid support.

DESCRIPTION OF THE SPECIFIC EMBODIMENTS

Improved rates are obtained in the binding between members of a specific binding pair, particularly where one of the members of the specific binding pair is bound to a solid support. In many situations measurement of such a rate provides useful information and is related to the presence and amounts of certain components in a medium. The rate can be measured directly as in a homogeneous system or it may be measured indirectly such as in a heterogeneous system.

For the most part, the methods in which the present invention is particularly useful involve assays, where competitive or non-competitive binding between members of a specific binding pair occurs. In the assay method one of the members of the specific binding pair—ligand or receptor—is conjugated to a label. This conjugate is one of the components of a signal producing system which provides for a detectable signal. The level of the observed signal is related to the amount of complex formation between the labels specific binding pair member and its reciprocal binding member.

For the purpose of this invention, a ligand is any organic compound which has a reciprocal binding member. Ligands will, therefore, be haptens and antigens, which include such diverse materials as small organic compounds, e.g., drugs, such as steroids, synthetic drugs, lipids, e.g., prostaglandins, leukotrienes, opiates, beta-andernergic drugs, or the like; saccharides or polysaccharides, such as cell walls; oligopeptides or proteins, such as enzymes, surface membrane proteins, structural proteins, hormones, or the like; nucleotides and polynucleotides.

The receptors will be compounds which recognize a particular spatial and polar conformation of the ligand. The receptors are usually macromolecules, generally having greater than 30,000 molecular weight, or usually having greater than 100,000 molecular weight, which may include natural receptors frequently found in surface membranes, or antibodies, or fragments thereof.

Either the ligand or the receptor may be an analyte in an assay medium.

A wide variety of labels may be involved, such as radionucleotides, enzymes, fluorescers, enzyme co-factors, enzyme substrates, etc.

Various methods are known for performing the assays which may enjoy the benefit of the subject invention. These methods may be "homogenous," which intends that there be no separation step, or "heterogeneous," which intends that there be a separation step. Illustrative methods for performing homogeneous assays may be found in U.S. Pat. No. 3,817,837, as well as U.S. Pat. Nos. 3,852,157, 4,190,496, 4,191,613, and 4,203,802 whose disclosures are incorporated herein by reference. Illustrative methods for heterogeneous assays may be found in U.S. Pat. Nos. 4,067,959, 4,168,146, and 4,299,916, which are incorporated herein by reference.

The homogeneous method normally involves combining in an aqueous medium labeled analyte or analyte analog with the sample and a receptor for the analyte, where binding of the receptor to the labeled analyte results in a change in signal. For example, where the label is an enzyme, binding the receptor to the analyte-enzyme conjugate normally results in substantially diminished enzyme activity.

As mentioned above, of particular interest for the subject invention is where one of the members of the specific binding pair is conjugated to a solid support, usually non-diffusibly conjugated to a non-dispersible solid support. This support can include a container surface, e.g., a microtiter well container, a plastic strip, a bibulous member, a micro-chromatographic column, a thin layer chromatographic strip, solid particles, or the like. The specific binding member may be conjugated to the support either covalently or non-covalently, normally depending upon the specific member, as well as the nature of the support.

A heterogeneous assay involving a solid support is illustrated by the use of a conventional dip-stick (solid strip). The dip-stick will have one of the members of a specific binding pair bound thereto. For example, either the analyte or the receptor may be bound to the dip-stick. In a preferred mode, an enzyme is also bound to the dip-stick, where the enzyme is one of a pair of enzymes, where the substrate of one enzyme is the product of the other enzyme. One introduces the dip-stick containing the various active members bound to the dip-stick into the assay medium containing the sample and any additional members necessary for production of a signal. For example, if the analyte is a hapten, one can also include receptor labeled with an enzyme. That receptor which does not bind to the hapten in the assay medium will bind to the hapten bound to the dip-stick. After sufficient time, one may remove the dip-stick from the assay medium and insert the dip-stick in a development solution which allows for production of a detectable signal. Usually, the dip-stick is partially immersed in the assay medium so that the active members are brought into contact with the sample.

To enhance the rate of reaction of the ligand and receptor to form the complex in an assay such as one described above, the assay medium may be subjected to ultrasonication such as by introduction into a bath in an ultrasonic device. Generally, the medium is subjected to ultrasonic sound for a time sufficient to allow for at least about 25% of the binding between the members of the specific binding pair to occur. The frequency of ultrasonication will vary from about 5 to $10^3$ kHz, preferably from about 15 to 500 kHz, depending upon the size of the bath, the time for the ultrasonication, and the available equipment. The power will generally be from about 10 to 100 watts, more usually from about 25 to 75 watts, and preferably from about 45 to 60 watts. The temperature will generally be maintained in the range of about 15° to 40° C. The assay medium will generally be a volume in the range of about 0.1 ml to 10 ml, usually from about 0.1 ml to 5 ml. The time may vary, depending on the frequency and power, from about 30 seconds to 2 hours, more usually from about 1 minute to 30 minutes. The power, frequency, and time will be chosen so as not to have a deleterious effect on the binding members and to assure accuracy of the assay.

It is found that the presence of a detergent in the sample can affect the response to the ultrasonic sound. Desirably, small amounts of non-ionic detergents or ionic detergents may be employed, generally being present in amounts of from 0.001 to 1 weight %, more usually in amounts of from about 0.005 to 0.1 weight %.

After the ultrasonic treatment, the remaining steps of the protocol for the assay may be performed.

The following examples are offered by way of illustration and not by way of limitation.

The rate of antigen-antibody immunoreactions with ultrasonication was compared to that with agitation mixing.

The apparatus employed for the ultrasonication was a Mettler Ultrasonic Cleaner, Model ME 11. The sample was submersed in a 1.1 liter container, at a 50 watt power setting and the ultrasonication maintained for various times. The frequency was 60 kHz. The agitation was in a mechanical shaker, Precision, GCG Model 50 set at 60 cycles per minute.

EXAMPLE I

Antibody to morphine (anti-morphine) was immobilized onto filter paper. A 5/16-inch disk of the antibody paper was incubated for 10-125 minutes with ultrasonincation or agitation mixing in a buffered 10 ng/ml morphine solution containing 1.0 ng/ml $H^3$-morphine. Following this, the disks were washed with phosphate buffer, pH7.0 and incubated in 1 ml of 0.1 M glycine-HCl buffer pH2.2, to release the bound morphine. The solution was then diluted to 10 ml with scintillation fluid encountered for $H^3$-morphine. The rate of the immunoreaction in reaching the 0.5 equilibrium point with ultrasonication was five times faster than that with agitation mixing in the antigen-antibody incubation between 5 and 10 minutes.

EXAMPLE II

Filter paper with glucose oxidase amine and antibody to penicilloic acid (anti-penicilloate) was fabricated into dip-sticks and indubated with a solution containing zero or 300 ng/ml ampicilloic acid and 200 ng/ml peroxidase-ampicilloic acid conjugte and the mixture ultrasonicated, or agitation mixed for 1-15 minutes at room temperature. The dip-stick was then transferred to a developer solution containing 300 mg/ml 4-Cl-1-napthol, 50 mM glucose and 2 mg/ml bovine serum albumin and 0.1 M phosphate buffer, pH7.0. After 15 minutes incubation in the developer, the dip-stick was removed and blotted and the color was measured with a reflectance colorimeter. Based on reflectometer units, at room temperature the reading for the sonic mixing was 60 after 1 minute and 115 after 10 minutes whereas the reading for the agitation mixing was 35 after 1 minute and 65 after 10 minutes.

It is evident from the above results that substantially enhanced rates of binding between ligands and receptors can be obtained, even where one of the members is bound to a solid surface, by employing ultrasonication for relatively short periods of time. In this manner, assays can be carried out with much greater repetitivity and greater sensitivity, since higher degrees of complexing will have occurred in relatively short periods of time. Furthermore, the ultrasonication does not adversely affect the dip-stick or the reagents in reducing their activity or causing other undesirable effects.

What is claimed is:

1. In a method for measuring the binding of members of a specific binding pair in an aqueous medium, the improvement which comprises ultrasonicating the medium containing the members of the specific binding pair for a sufficient time to enhance the rate of binding of said members.

2. The method of claim 1 wherein the members of the specific binding pair are ligand and receptor.

3. The method of claim 1 wherein the medium is ultrasonicated at a frequency of about 5 to $10^3$ kHz 4. The method of claim 1 wherein the medium is ultrasonicated for a period of about 30 seconds to 2 hours.

5. The method of claim 1 wherein the medium is ultrasonicated at a temperature of about 15° to 40° C.

6. The method of claim 1 wherein the medium further contains a signal producing system capable of producing a detectable signal which is dependent on the binding of the members of the specific binding pair.

7. The method of claim 1 wherein one of the members of the specific binding pair is bound to a support.

8. In an assay method for determining the presence in a sample of a first member of a specific binding pair wherein the sample is combined in an aqueous medium with at least a second member of the specific binding pair and components of a signal producing system capable of producing a detectable signal in relation to the amount of said first member, the improvement which comprises ultrasonicating the mixture for a time and at an intensity sufficient to enhance the rate of the binding of the members of the specific binding pair.

9. The method of claim 8 wherein the members of the specific binding pair are ligand and receptor.

10. The method of claim 9 wherein the ligand is a hapten.

11. The method of claim 9 wherein the ligand is an antigen.

12. The method of claim 9 wherein the receptor is an antibody.

13. The method of claim 8 wherein the medium is ultrasonicated at a frequency of about 5 to $10^3$ kHz 14. The method of claim 8 wherein the medium is ultrasonicated for a period of about 30 seconds to 2 hours.

15. The method of claim 8 wherein the medium is ultrasonicated at a temperature of about 15° to 40° C.

16. The method of claim 8 wherein one of the components of the signal producing system is an enzyme conjugated to one of the members of the specific binding pair.

17. The method of claim 8 wherein one of the components of the signal producing system is a fluorescer conjugated to one of the members of the specific binding pair.

18. The method of claim 8 wherein one of the members of the specific binding pair is bound to a support.

19. The method of claim 18 wherein the support is a solid strip.

20. The method of claim 8 wherein at least one of the components of the signal producing system is bound to a dip-stick.

21. The method of claim 8 wherein components of the signal producing system comprise an enzyme bound to said dip-stick and a second enzyme where the substrate of one enzyme is the product of the other enzyme.

22. The method of claim 8 wherein the member of a specific binding pair in the sample is a protein.

* * * * *